US011099172B2

(12) United States Patent
Akassoglou et al.

(10) Patent No.: US 11,099,172 B2
(45) Date of Patent: Aug. 24, 2021

(54) IN VITRO ASSAYS FOR INHIBITION OF MICROGLIAL ACTIVATION (71) Applicants: The J. David Gladstone Institutes, a testamentary trust established under the Will of J. David Gladstone, San Francisco, CA (US); The Regents of the University of California, Oakland, CA (US)

(72) Inventors: Katerina Akassoglou, San Francisco, CA (US); Michelle Arkin, San Francisco, CA (US); Kean-Hooi Ang, San Francisco, CA (US); Anke Meyer-Franke, San Francisco, CA (US); Christopher Wilson, San Francisco, CA (US)

(73) Assignees: The J. David Gladstone Insitutes, San Francisco, CA (US), a testamentary trust established under the Will of J. David Gladstone; The Regents of the University of California, Oakland, CA (US)

( * ) Notice: Subject to any disclaimer, the term of this patent is extended or adjusted under 35 U.S.C. 154(b) by 149 days.

(21) Appl. No.: 15/943,474

(22) Filed: Apr. 2, 2018

(65) Prior Publication Data
US 2019/0064152 A1 Feb. 28, 2019

Related U.S. Application Data (63) Continuation of application No. 15/109,163, filed as application No. PCT/US2015/010769 on Jan. 9, 2015, now abandoned.

(60) Provisional application No. 61/926,314, filed on Jan. 11, 2014.

(51) Int. Cl.
*G01N 33/50* (2006.01)
(52) U.S. Cl.
CPC ....... *G01N 33/5058* (2013.01); *G01N 33/502* (2013.01); *G01N 33/5008* (2013.01); *G01N 33/5014* (2013.01); *G01N 33/5044* (2013.01); *G01N 33/5047* (2013.01); *G01N 2500/00* (2013.01); *G01N 2800/28* (2013.01); *G01N 2800/7095* (2013.01)

(58) Field of Classification Search
None
See application file for complete search history.

(56) References Cited

U.S. PATENT DOCUMENTS 7,807,645 B2  10/2010  Akassoglou
8,198,234 B2   6/2012  Laskowitz
8,841,326 B2   9/2014  Vander Jagt
2009/0304712 A1 12/2009 Takeuchi et al.
2017/0003280 A1  1/2017 Akassoglou et al.

FOREIGN PATENT DOCUMENTS

EP          3092496 A1     11/2016
EP          3092496 B1      5/2020
WO     WO 200123886        4/2001
WO     WO 2007038407       4/2007
WO     WO-2015106066 A1    7/2015

OTHER PUBLICATIONS

Adams et al. (2007) "The fibrin-derived gamma377-395 peptide inhibits microglia activation and suppresses relapsing paralysis in central nervous system autoimmune disease"; J Exp Med ;204(3): pp. 571-582).
Beutner et al (2010) "Generation of microglial cells from mouse embryonic stem cells"; Nat Protoc., 5(9): pp. 1481-1494.
Block and Hong (2007) "Chronic microglial activation and progressive dopaminergic neurotoxicity"; Biochem Soc Trans.; 35: pp. 1127-1132.
Boillee et al., (2006) "Onset and progression in inherited ALS determined by motor neurons and microglia"; Science, 312(5778): pp. 1389-1392.
Giulian and Baker (1986) "Characterization of ameboid microglia isolated from developing mammalian brain"; J Neurosci., 6(8): pp. 2163-2178.
Hansen et al. A Versatile High Throughput Screening System for the Simultaneous Identification of Anti-Inflammatory and Neuroprotective Compounds. Journal of Alzheimer's Disease. May 20, 2010, vol. 19, No. 2; pp. 437-450.
Horvath, et al (2008) "Differential migration, LPS-induced cytokine, chemokine, and NO expression in immortalized BV-2 and HAPI cell lines and primary microglial cultures"; J Neurochem.,107(2): pp. 557-569.
Lull and Block (2010) "Microglial activation and chronic neurodegeneration" Neurotherapeutics. 7(4): pp. 354-365.
Lynch (2009) "The multifaceted profile of activated microglia"; Mol Neurobiol.;40(2): pp. 139-156.
Morioka et al (1993) "Characterization of microglial reaction after middle cerebral artery occlusion in rat brain."; J Comp. Neurol, 327(1): pp. 123-132).
Nagai, et al (2005) "Immortalized human microglial cell line: phenotypic expression"; J Neurosci. Res.,. 81(3): pp. 342-348.
Ohsawa et al (1997) "Generation and characterization of a microglial cell line, MG5, derived from a p53-deficient mouse"; Glia, 21(3): pp. 285-298.
Palazzi and Monti (2010) "Microglia and neuroprotection: from in vitro studies to therapeutic applications"; Prag. Neurobiol, 92(3): pp. 293-315.
Piers, TM. Fibrin and Fibrinogen Pathways in Microglia Fibrinogen-Induced Signalling-Implications for Neurodegeneration. Doctoral Thesis, University College London. 2012; pp. 1-403. obtained online <http://discovery.ucl.ac.uk/1344077 />.

(Continued)

*Primary Examiner* — Vera Afremova
(74) *Attorney, Agent, or Firm* — Schwegman Lundberg & Woessner, P.A.

(57) ABSTRACT

The present invention provides cell-based assays, including high throughput cell-based assays, for identification of candidate therapeutic agents with the ability to inhibit microglial activation in vivo in response to different ligands.

6 Claims, 9 Drawing Sheets

(56) References Cited

OTHER PUBLICATIONS

Stansley et al (2012) "A comparative review of cell culture systems for the study of microglial biology in Alzheimer's disease"; J Neuroinflammation, 9, pp. 115.
"U.S. Appl. No. 15/109,163, Final Office Action dated Jul. 5, 2018", 10 pgs.
"U.S. Appl. No. 15/109,163, Non Final Office Action dated Oct. 2, 2017", 11 pgs.
"U.S. Appl. No. 15/109,163, Preliminary Amendment filed Jan. 5, 2017", 7 pgs.
"U.S. Appl. No. 15/109,163, Response filed Apr. 2, 2018 to Non Final Office Action dated Oct. 2, 2017", 6 pgs.
"European Application Serial No. 15735033.1, Extended European Search Report dated Jul. 13, 2017", 6 pgs.
"International Application Serial No. PCT/US2015/010769, International Preliminary Report on Patentability dated Jul. 21, 2016", 7 pgs.
"International Application Serial No. PCT/US2015/010769, International Search Report dated Mar. 25, 2015", 3 pgs.
"International Application Serial No. PCT/US2015/010769, Written Opinion dated Mar. 25, 2015", 5 pgs.

IN VITRO ASSAYS FOR INHIBITION OF MICROGLIAL ACTIVATION

GOVERNMENT SUPPORT

This invention was made with government support under Grant NS052189 awarded by the National institutes of Health. The United States Government has certain rights in this invention.

FIELD OF THE INVENTION

The present invention relates to the field of compositions and in vitro assays for the identification of agents for the prevention and treatment of pathological conditions associated with inflammation and/or neuronal injury.

BACKGROUND OF THE INVENTION

In the following discussion certain articles and methods will be described for background and introductory purposes. Nothing contained herein is to be construed as an admission of prior art. Applicant expressly reserves the right to demonstrate, where appropriate, that the articles and methods referenced herein do not constitute prior art under the applicable statutory provisions.

Microglia, the resident innate immune cells in the brain, have long been implicated in the pathology of neurodegenerative diseases. Neurodegenerative diseases (ex. Alzheimer's Disease, Parkinson's Disease, Huntington's Disease, ALS, etc.) share common characteristics, such as changes in microglial number and morphology, elevated cytokine levels, oxidative stress, and progressive neuronal loss. Increasing evidence reports that microglia can become a chronic source of cytokines and active oxygen (ROS) that drive progressive neuron damage and are implicated in the chronic nature of neurodegenerative diseases. Block M L and Hong J S. *Biochem Soc Trans.* 2007; 35:1127-1132.

Microglia can become chronically activated by either a single stimulus, e.g., Lipopolysaccharide ("LPS") stimulus or neuron damage, or by multiple stimuli exposures to result in cumulative neuronal loss over time. Activated microglia produce toxic factors (cytokines and reactive oxygen species) following either single or chronic exposure to disease proteins, environmental toxins, cytokines, and neuronal damage, resulting in the progressive loss of neurons over time, a fundamental component of neurodegenerative disease. Lull M E and Block M L, *Neurotherapeutics.* 2010 October; 7(4): 354-365. Recent work suggests that redox signaling in microglia may be a critical mechanism of chronic neuroinflammation, and certain cells may be inherently vulnerable to reactive microgliosis id. While the mechanisms driving these phenomena are just beginning to be understood, the microglial response to neuron damage ("reactive microgliosis") and ROS have been implicated as key mechanisms of chronic and neurotoxic microglial activation.

There is thus a need in the art for a method of identifying candidate therapeutic agents with the ability to inhibit such microglial activation in pathologies associated with neuronal injury. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides cell-based assays, including high-throughput cell-based assays, for identification of candidate therapeutic agents with the ability to inhibit microglial activation in vivo.

In one embodiment, the invention provides a cell-based assay for identification of candidate therapeutic agents that inhibit microglia activation in vivo, comprising providing in vitro activated microglial cells, contacting said activated microglial cells with one or more test agents, identifying one or more test agents that exhibit inhibition of the in vitro microglia activation, and determining toxicity of the identified test agents that exhibit inhibition of the in vitro microglia activation by determination of cell death upon exposure of the test agents to the microglial cells. The test agents that exhibit inhibition of the in vitro microglia activation, and lack of toxicity, are candidate therapeutic agents for the inhibition of microglial cell death.

The extent of microglial activation in the invention can be measured on a percentage basis, and thus agents with a particular percentage level of inhibition of microglial activation can be identified. In the particular examples of the invention, agents are identified with at least a 50% level of inhibition of microglial activation using the cell-based assay of the invention. The stringency of such inhibition can be increased or decreased depending upon the specific criteria and parameters applied to an experiment using the cell-based assays. Thus, although the identified candidate therapeutic agents described herein were identified based on the criteria of 50% or greater inhibition of microglial activation in the cell-based assays of the invention, a person of skill in the art could also identify candidate therapeutic agents that have either higher or lower levels of inhibition of microglial activation, as demonstrated in the examples and accompanying figures herein.

The invention also provides high-throughput cell-based assays for identifying a candidate therapeutically active agent for clinical inhibition of microglia activation, comprising the steps of providing a panel of in vitro activated microglial cells, contacting said panel of microglial cells with one or more individual test agents, determining whether the test agents cause inhibition of the activation of the microglial cells treated with the test agents, and determining the level of cell death of the microglial cells treated with the test agents, where the one or inure test agents that exhibit inhibition of the activation of the microglial cells and no increased cell death are candidate therapeutically active agents.

The microglial cells used in the assays of the invention may be primary microglia or they may be cells from an immortalized microglia cell line that display the requisite physiological attributes for use in the cell-based assays. The microglia used in the assays of the invention may be activated using a variety of in vitro mechanisms. This includes activation of microglia by in vitro exposure to activators of microglia, e.g., soluble ligands or immobilized substrates, including binding partners of CD11b/CD18 and TLR4. For example, in some aspects, the microglial cells are activated by in vitro exposure to an active fibrin composition. In another example, the microglial cells are activated by in vitro exposure to LPS, a gram negative bacterial immunostimulant that triggers a cascade of proinflammatory events that mimic pathological responses. It will be apparent to one skilled in the art upon reading the present invention that various mechanisms of activating microglial cell in vitro can be used with the cell-based assays of the present invention.

The activation of the microglia in the cell-based assay of the invention may be determined using a number of biochemical and morphological end points. For example, microglial activation may be measured using gene expression, e.g., increased expression of TNF, IL-1, Clex10, Cel5, IL-10 and/or Mcp-1. In another example, microglial activation can be identified through size of the microglia, with activated microglia generally having a surface area of $\geq 800$ $\mu m^2$.

Preferably, the assays of the invention also measure the toxicity of test agents to identify candidate therapeutic agents that inhibit microglia activation but which do not cause microglia cell death. Toxicity through cell death can be identified in the assay, e.g., by identification of the hallmark apoptotic DNA ladders or by morphological changes, such as shrinkage of the cell surface area of the microglia. In one specific aspect, cell death is identified in the cell-based assays through shrinkage of the cell surface area of the microglia to 150 $\mu m^2$ or less.

Various test agents can be used in the cell-based assays of the present invention. In some embodiments, the test agents used in the screening are agents with demonstrated affinity to targets involved in microglia activation. In other embodiments, the test agents used in the screening are agents with no known activity or identified binding target. In still other embodiments, the test agents used in the screening are agents that comprise known drugs with clinical evaluation data. In still other embodiments, the test agents used in the screening are agents that comprise known anti-inflammatory and microglia-macrophage response modulators.

One advantageous feature of the assays of the present invention is the ability of the assays to identify ligand-selective inhibitors of microglial activation in a high throughput fashion.

Another feature of the invention is that the cell-based assays allow direct comparisons of compound selectivity of the various agents tested for inhibition of microglia activation.

Another advantage of the assays of the invention is that they can be used to screen different classes and varieties of agents, including antibody, peptide or small molecule libraries.

These assays can be used in primary screens to discover novel inhibitors of innate immunity, as well as in secondary screens to assess ligand specificity or to provide additional data on the predicted functional activity of the test agents in an in vivo setting for therapeutic use.

Yet another feature of the invention is the ability to utilize morphologic activation characteristics as the outcome measure of the assays. All prior methods of identification of ligand-selective inhibitors were either based on adhesion of cell lines or non-cellular assays with little predictive value for in vivo efficacy. Such inhibition of morphologic activation in vitro has been shown to have predictive value for in vivo efficacy (Adams R A et al., *J Exp Med*, 2007 Mar. 19; 204(3):571-82).

An advantage of the cell-based assays of the invention are that they are well suited for a high throughput screening (HTS) system, and the invention has demonstrated that the assay can be fully automated using 96 or 384-well plates.

DETAILED DESCRIPTION OF THE INVENTION

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Harlow and Lane, *Antibodies, A Laboratory Manual*, Cold Spring Harbor Publications, New York, 1988; Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); *Lehninger, Principles of Biochemistry*, $3^{rd}$ Ed., W.H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and, "the" include plural referents unless the context clearly dictates otherwise. Thus, for example, reference to "a test agent" refers to one, more than one, or mixtures of such agents, and reference to "a method" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The term "antibody" is intended to include any polypeptide chain-containing molecular structure with a specific shape that fits to and recognizes an epitope, where one or more non-covalent binding interactions stabilize the complex between the molecular structure and the epitope. As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Where bispecific antibodies are to be used, these may be conventional bispecific antibodies, which can be manufactured in a variety of ways (Holliger and Winter, *Curr Opin Biotechnol.* 1993 August; 4(4):446-9), e.g., prepared chemically or from hybrid hybridomas, or may be any of the bispecific antibody fragments mentioned above. It may be preferable to use scFv dimers or diabodies rather than whole antibodies. Diabodies and scFv dimers can be constructed without an Fe region, using only variable domains, potentially reducing the effects of anti-idiotypic reaction. Other forms of bispecific antibodies include the single chain "Janusins" described in Traunecker A et al., *EMBO J.* 1991 December; 10(12):3655-9. Such antibodies also include CRAbs, which are chelating antibodies which provide high affinity binding to an antigen, D. Neri, et al. *J. Mol. Biol,* 246, 367-373, and dual-variable domain antibodies as described in Wu C et al., *Nat Biotechnol.* 2007 November; 25(11):1290-7. Epub 2007 Oct. 14.

The term "microglial activation" as used herein can refer to processes associated with innate activation or adaptive activation of the microglia. Such activation may include morphological changes of the microglial cells, including shortening of cellular processes and enlargement of their soma, as well as the release of proinflammatory cytokines and chemokines, reactive oxygen and/or nitrogen intermediates, proteinases and complement proteins, and upregulation of cell surface activation antigens.

The term "neurodegeneration" refers to a physiological state caused by neuronal injury associated with neuronal loss and/or damage. In specific aspects, neurodegeneration refers to neuronal injury resulting in impaired cognitive function.

The term "neuronal injury" as used herein refers to any damage or dysfunction exhibited by neurons, including hut not limited to loss of myelin, dendrite retraction, dendritic spine density reduction, axonal damage and neuronal death. A "neuronal condition" as used herein refers to any damage or dysfunction exhibited by neurons, including but not limited to dendrite retraction, dendritic spine density reduction, axonal damage and neuronal death.

The term "pharmaceutically acceptable carrier" as used herein is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents is well known in the art. Except insofar as any conventional media or agent is incompatible with the agents provided herein, use thereof in the composition is contemplated.

The terms "peptide," "polypeptide," and "protein" are used interchangeably herein, and refer to a polymeric form of amino acids of any length, which can include coded and non-coded amino acids, chemically or biochemically modified, labeled or derivatized amino acids, and polypeptides having modified peptide backbones.

The term "peptidomimetic" as used herein refers to a protein-like chain designed to mimic a peptide. They typically arise from modification of an existing peptide in order to alter the molecule's properties. For example, they may arise from modifications to change a molecule's stability, biological activity, or bioavailability.

The term "pharmacophore" is used herein in an unconventional manner. Although the term conventionally means a geometric and/or chemical description of a class or collection of compounds, as used here the term means a compound that has a specific biochemical activity or binding property conferred by the 3-dimensional physical shape of the compound and the electrochemical properties of the atoms making up the compound. Thus, as used here the term "pharmacophore" is a compound and not a description of a collection of compounds which have defined characteristics. Specifically, a "pharmacophore" is a compound with those characteristics.

The term "small molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

A "test agent" as used herein refers to any agent that is a candidate to treat a disease or symptom thereof. Such agents include, but are not limited to, peptides; proteins (including derivatized or labeled proteins); antibodies or fragments thereof; small molecules; aptamers; carbohydrates and/or other non-protein binding moieties; derivatives and fragments of naturally-occurring binding partners; peptidomimetics; and pharmacophores.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in an animal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The Invention in General

The present invention is based on the novel development of a composition that mimics the biochemical and proinflammatory properties of fibrin matrices found in vivo during pathological conditions in an in vitro setting. These fibrin compositions are highly reproducible in activity, and provide the advantage of essentially mimicking the in vivo activity of fibrin, and use of such compositions in assays enable the screening of fibrin inhibitors that have a higher likelihood of being efficacious in clinical use. More particularly, by using a fibrin composition with similar properties of fibrin in vivo activity observed in pathological conditions, the probability of finding biologically active inhibitors with in vivo efficacy is enhanced.

Microglia are activated in response to injury and immunological stimuli, and in doing so undergo dramatic alterations in morphology. See, e.g., Kreutzberg G W, *Trends Neurosci.* 1996; 19:312-318. It has been shown, however, that changes in morphology alone are unlikely to allow a differentiation between microglial activation in response to normal, physiological changes and toxic microglial activation associated with pathological states such as neurodegeneration. Lynch M A. *Mol Neurobiol.* 2009; 40:139-156. In reacting to extracellular signals, such as the presence of pathogens, foreign material and dead or dying cells, microglia may undergo a morphological change into an amoeboid shape with short or non-existent processes. This morphological change is also accompanied by changes in signaling and gene expression that can result in changes in surface receptor expression, the release of pro- or anti-inflammatory factors, recruitment molecules, and ROS, among others. The cumulative effect of these changes in morphology and phenotype is a shift from resting to activated microglia.

Although microglia and macrophages are different cell types, they share several common pro-inflammatory pathways. Therefore the cell-based assays of the invention can also be used in the discovery of inhibitors for macrophage activation.

The central aim of the present invention was to provide a novel high-content, high throughput assay that could measure the activation of primary microglia in response to activators such as LPS, or other activators (e.g. fibrin, complement, amyloid) in a format that would allow efficient and large-scale screening, e.g., of small molecule and/or antibody libraries.

In designing the high throughput screening assays of the invention, fibrin and LPS were selected as two ligands that activate microglia through different receptors, CD11b/CD18 and TLR4, respectively. Microglia cells will change morphology upon activation by LPS, including retracting cell processes and becoming amoeboid, with a several fold increase in cell surface area. This morphological change upon activation allows the development of a fully automated high content HTS that uses microglial cell surface area measurement as a quantification of activation of microglia.

A significant increase in cell size is one of the most prominent features of microglia activation and correlates with increased pro-inflammatory activity. The inventors developed a fluorescent assay for quantification of changes in microglial cell size and used the INCell Analyzer 2000™ instrument (GE Healthcare, San Francisco, Calif.) for image acquisition and analysis. The assay was adapted to a 96-well format to evaluate assay conditions and automated image acquisition analysis with the INCell instrument and software and then miniaturized to a 384-well plate format, using fully automated coating of the microglial activating agent (e.g., fibrin), plating of microglia cells, addition of compounds, addition of activator (e.g., LPS), as well as the components for the fixation and staining procedures necessary for consistent measurement of cell morphology. The protocol for the isolation of rat primary microglia yield enough cells for seven to eight 384 well assay plates per litter of rat pups.

Primary Screening of Test Agents

The cell-based assays of the invention can be used to identify test agents such as small-molecule or monoclonal antibody inhibitors of microglial cell activation that act through various targets and mechanisms. By measuring phenotypic cell end points rather than e.g., binding to a specific target or modulation of expression of a particular gene, identification of test agents that may modulate complex pathways and/or target the effects of multiple pathways or targets simultaneously can be performed. Thus, in cases where the underlying biological mechanisms are not yet fully understood, such as neurodegenerative diseases, the ability to identify the inhibition of biological processes such as microglial activation provides a significant advantage over purely biochemical assays.

In certain embodiments, the library of test agents used for screening in the cell-based assays of the invention is from a focused library of agents with known anti-inflammatory properties or known to modulate microglial/macrophage response. Such molecules may not be confirmed as target-based agents, but may provide an enriched population of agents with the potential of having a physiological effect on microglia activation.

Secondary Screening in Target-Based Drug Discovery

The cell-based assays of the invention can also play a critical role in target-based drug discovery as confirmatory functional assays for compounds identified by primary biochemical screening. If a target is known to be involved in the activation of microglia, a phenotypic assay such as those described herein would allow testing the effects of the agents that have demonstrated affinity to such targets in a physiologically relevant context. Following identification of an inhibitor of a target identified as involved or potentially involved in the activation of microglia, a cell-based assay of the present invention allows confirmatory testing of these test agents in a biological context.

Cells for Use in the Assays of the Present Invention

The cells for use in the assays of the invention include primary microglia cells and immortalized cell lines. Rodent cell lines that are useful in the assays of the invention include, but are not limited to, BV-2, C8-B4, N9, N11, various EOC lines, highly aggressive proliferating immortalized (HAPI) cell lines, and MG5. Horvath, R J et al., *J. Neurochem.* 2008, 107, 557-569; Ohsawa, K. et al. *Glia* 1997, 21, 285-298; Stansley, B et al. *J. Neuroinflammation* 2012, 9, 115. Human immortalized microglial cell lines, such as HMO6 may be preferred for certain neurotherapeutic studies, as their phenotype is more closely related to primary human microglia, Nagai, A et al., *J. Neurosci. Res.* 2005, 81, 342-348.

Experimental evidence shows that compared with cell lines, primary microglial cells more closely resemble both the phenotype and the stimulus responses of microglial cells in vivo. Stansley et al., Id. One exemplary method for obtaining a population of primary microglial cells consists of establishing a confluent mixed glial culture from the brains of neonate rodents. Isolation of the microglia can be accomplished by culturing the primary cells and collecting the detached cells. Giulian, D and Baker, T J *J. Neurosci.* 1986, 6, 2163-2178.

More recently, it has been possible to produce microglial cells from stem cells using a modified neuronal differentiation method. Beutner, C et al. *Nat Protoc.* 2010, 5, 1481-1494. Microglia may also be isolated from human iPS cells. From a pathophysiological point of view, these microglial cells are more relevant than immortalized cell lines due to their similarity to freshly isolated primary microglia, essentially displaying indistinguishable morphology, functions, and cellular markers. Since this cell source potentially offers an unlimited supply of microglia generated in vitro, this may be a particularly attractive cell source for the high throughput screening assays of the present invention.

Microglia Activation in Neurodegenerative Disorders

As the brain's resident macrophage, microglial cells play a key role in protection against exogenous and endogenous insults. Disruption of brain homeostasis caused by physiological or pathological conditions induces microglial cell activation and the release of cytokines, chemokines, and toxins that lead to inflammation. This appears to be a common process in a number of acute and chronic neurodegenerative diseases such as stroke (Morioka, T et al., *J. Comp. Neural.* 1993, 327, 123-432), Alzheimer's disease (Gao, H M and Hong, J S, *Trends Immunol.* 2008, 29, 357-365), Parkinson's disease (McGeer, P L et al., *Neurology* 1988, 38, 1285-1291), Multiple sclerosis (McGeer, P L et al., *Neurology* 1988, 38, 1285-1291), ALS (Banati, et al., *Clin. Neuropathol.* 1995, 14, 197-200), Huntington disease (Moller, T. *J. Neural Transm.* 2010, 117, 1001-1008), and HAND (Zindler, E and Zipp, F *Best Pract. Res. Clin. Anaesthesiol.* 2010, 24, 551-562). Microglial activation can induce or exacerbate such neuronal damage, and postmortem analyses of human tissues and animal models of slow progressing neurodegenerative diseases have shown neuronal loss in conjunction with increased levels of activated microglia in areas of the brain with lesions. Polazzi, E and Monti, B. *Prog. Neurobiol.* 2010, 92, 293-315; Boillee, S et al., *Science* 2006, 312, 1389-1392. The cell-based assays of the invention thus may be particularly useful to identify candidate therapeutic agents for the treatment of such disorders.

Test Agents for Screening Using the Assays of the Invention

The assays of the invention are used to identify candidate therapeutic agents for the modulation of microglial activation in vivo. This includes the testing of new agents as well as assays to test known compounds (including synthetic, recombinant or naturally-occurring compounds) for their effect on microglial activation and/or cell death.

It is known in the pharmaceutical arts that binding affinity to a target and efficacy do not necessarily correlate, and that identification of cell-based activity changes conferred by a test agent is an improved functional predictor of therapeutic activity compared to agents identified merely by affinity, e.g., binding of agents to microglial receptors.

In certain aspects, the assays of the invention correlate with in vivo modulation of signaling through activated fibrin. Examples of cell-based assays for use with the present invention include, but are not limited to, high throughput binding screening; assays to measure cell activation, proliferation, necrosis and/or apoptosis; flow cytometry assays; metabolic assays measuring labeling or turnover; phase and fluorescence microscopy; receptor phosphorylation and/or turnover; cell signaling assays; immunohistochemistry studies; reporter gene assays, and subcellular fractionation and localization. More specific examples of such assays are: FLIPR to detect changes in intracellular calcium concentration and cell-based ELISA assays to detect and quantify cellular proteins including post-translational modifications associated with cell activation.

Biochemical assays can also be used to correlate binding with efficacy in the cell-based assay methods of the invention. These include, but are not limited to, spectrophotometric assays, fluorometric assays, calorimetric assays, chemiluminescent assays, radiometric assays, chromatographic assays, colorimetric assays, and substrate specificity inhibitor kinase assays. Specific examples are: luciferase assays, in which firefly luciferase protein catalyzes luciferin oxidation and light is generated in the reaction, and which is frequently used as a reporter gene for measuring promoter activity or transfection efficiency; electrophoresis; gas-liquid chromatography; and Forster resonance energy transfer (FRET).

To confirm the functional activity of a test agent, a therapeutically effective amount of a test agent of the invention may be administered to a subject (including an animal model of a neurological pathology) to confirm its in vivo activity following identification in an assay of the invention. By "therapeutically effective dose or amount" or "effective amount" is meant an amount of the test agent that, when administered, brings about a positive therapeutic response with respect to neuronal injury. In some embodiments of the invention, the therapeutically effective dose is in the range from about 0.1 µg/kg to about 100 mg/kg body weight, about 0.001 mg/kg to about 50 mg/kg, about 0.01 mg/kg to about 30 mg/kg, about 0.1 mg/kg to about 25 mg/kg, about 1 mg/kg to about 20 mg/kg, about 3 mg/kg to about 15 mg/kg, about 5 mg/kg to about 12 mg/kg, about 7 mg/kg to about 10 mg/kg or any range of value therein. It is recognized that the method of treatment may comprise a single administration of a therapeutically effective dose or multiple administrations of a therapeutically effective dose.

The test agent is administered to supply a desired therapeutic dose to promote a desired therapeutic response of the modulator to the therapeutic area. By "desired therapeutic response" is intended an improvement in the condition or in the symptoms associated with the condition, including the inhibition of angiogenesis.

The test agents can be formulated in a unit dosage such as a solution, suspension or emulsion, in association with a pharmaceutically acceptable carrier. Such carriers are inherently nontoxic and nontherapeutic. Examples of such carriers are saline, Ringer's solution, dextrose solution, and Hanks' solution. Nonaqueous carriers such as fixed oils and ethyl oleate may also be used. The vehicle may contain mine amounts of additives such as substances that enhance chemical stability, including buffers and preservatives.

Various methods of delivery can be used to deliver the test agent, and will in part be dependent upon the agent and its bioavailability. For example, small molecules or other agents that are bioavailable may be administered orally, whereas protein-based agents are generally but not exclusively administered parenterally. Certain agents may be administered systemically, while others may be more beneficial with a local delivery. The method of delivery will be apparent to one skilled in the art upon reading the specification, and can be determined in view of the specific properties of the test agent.

It is understood that the effective amount of a test agent may vary depending on the nature of the effect desired, frequency of treatment, any concurrent treatment, the health, weight of the recipient, and the like. See, e.g., Berkow et al., eds., *Merck Manual,* 16th edition, Merck and Co., Rahway, N.J. (1992); Goodman et al., eds., *Goodman and Gilman's The Pharmacological Basis of Therapeutics,* 8th edition, Pergamon Press, Inc., Elmsford, N.Y. (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston (1985), Katzung, *Basic and Clinical Pharmacology,* Appleton and Lange, Norwalk, Conn. (1992), which references and references cited therein, are entirely incorporated herein by reference.

The test agent may be contained in a pharmaceutically-acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical. Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents for delivering cells is well known in the art. Except insofar as any conventional media or agent is incompatible with the cells or polypeptides provided herein, use thereof in the compositions is contemplated. Supplementary active compounds can also be incorporated into the test agents.

For confirming in vivo activity, a composition comprising a test agent is formulated to be compatible with its intended route of administration. Examples of routes of administration include intravenous, intraarterial, intracoronary, parenteral, subcutaneous, subdermal, subcutaneous, intraperitoneal, intraventricular infusion, infusion catheter, balloon catheter, bolus injection, direct application to tissue surfaces during surgery, or other convenient routes.

Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Test agents suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent possible. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents.

Prolonged absorption of the injectable compositions can be brought about by including in the composition an agent which delays absorption, for example, aluminum monostearate and gelatin. Sterile injectable solutions can be prepared by incorporating an active agent in the required amount in an appropriate solvent with a selected combination of ingredients, followed by filter sterilization. Generally, dispersions are prepared by incorporating an active agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. In many cases, it will be preferable to include isotonic agents.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1

Isolation and Culture of Microglia Cells

Rat cortices were dissected from 2-3 postnatal day (P) old rat pups and transferred into Dulbecco's Phosphate Buffered Saline (DPBS), containing glucose and sodium-pyruvate (Life Technologies/GIBCO, Grand Island, N.Y.). The meninges were removed and the cortices transferred into 7.5 ml of the same DPBS (10 cortices) and minced with a sterile razor blade. Tissue pieces with DPBS were transferred into a 15 ml tube, 1.5 ml of 2.5% Trypsin solution (10× Trypsin, Life Technologies/GIBCO, Grand Island, N.Y.) and 500 µl of DNAse (SIGMA, D4513, 2000 Kunitz units/rap were added.

Following incubation at 37° C. for 25 minutes, the trypsin solution was removed, cortices were washed with 30% Fetal Bovine Serum (FBS) in DPBS and serially triturated with a 5 ml pipette with 7 ml of 30% FBS in DPBS containing DNAse (1000 Kunitz units). The cell suspension was gently spun at 200×g for 15 minutes and the pellet re-suspended in DMEM (Life Technologies/GIBCO, Grand Island, N.Y.), containing 10% heat-inactivated FBS (Life Technologies/GIBCO, Grand Island, N.Y.; lots pre-tested for microglia survival), 100 units/ml Penicillin and 100 mg/ml Streptomycin (100× solution, Life Technologies/GIBCO, Grand Island, N.Y.). Cells are plated into Poly-D-lysine pre-coated T-75 flasks in 15 ml of medium, 2-3 cortices per flask. Cells were incubated at 37° C. in a humidified 5% CO2 incubator. On day 3 in vitro, 5 ml of fresh medium were added and cells were grown for one more day.

On day 4 in vitro, flasks were placed onto a shaker platform, pre-heated to 37° C. and microglia cells were shaken off the cortical cell layer at 200 rpm for 2 hours. The medium containing mostly microglia cells was removed from the flasks and cells are spun at 200×g for 15 minutes. The cell pellets were gently re-suspended in 200 µl of culture medium per pellet first to prevent cell clumping, then combined into one tube and further diluted to 10 ml. After counting the number of cells with a hematocytometer, the cell concentration was adjusted to approximately 5000 cells/µL. The yield per rat cortex should amount to approximately $2.5 \times 10^6$ microglia cells.

Example 2

Production of Fibrin Assay Plates

A 6 µg/ml fibrin solution was used to coat the wells of a 384-well plate. Microglia cells were further diluted with culture medium to 6,000/50 µl per well and plated either onto the fibrin-coated wells of a test 384-well plate, or onto Poly-D-Lysine pre-coated black-walled 384-well plates (µclear, LPS assay, Greiner, BioOne, Germany), using the Thermo Scientific Matrix WellMate™ instrument at a medium speed setting (Thermo Scientific, Waltham, Mass.).

One hour after plating, 100 nl of compounds were added to each well from 10 mM stock solutions in DMSO to a 10 µM final concentration, using a Biomek® automated laboratory workstation (Beckman-Coulter, Brea, Calif.). 50 µl of a 1 ng/ml solution of LPS, a known microglia activator, was added 1 hour after the addition of compounds, to a final concentration of 500 pg/ml, using the BioTek E1-406™ liquid handling system (Thermo Fisher, Waltham, Mass.). The liquid was added against the wall of each well to prevent dislodging of cells from the well surface. Cells were transferred to a 37° C., 5% $CO_2$ incubator for 48 hours.

50 µl of medium were removed from each well and 50 µl of 8% Paraformaldehyde were added using the BioTek E1-406™ liquid handling system. After incubation for 1 hour all liquid (100 µl) was removed and wells were washed 3 times with 100 µl of DPBS with calcium and Magnesium (Life Technologies/GIBCO, Grand Island, N.Y.). 50 µl of a 0.1% Triton-x-100 solution in DPBS was added and incubated for 1 hour. After incubation, wells are washed 3 times with DPBS, 50 µl of DPBS containing 0.5 µg/ml CellMask™ Red Stain and 2 µg/ml Hoechst nuclear dye (Life Technologies/Invitrogen, Grand Island, N.Y.) are added and incubated for 1 hour.

Example 3

Assay Segmentation of Activated and Dead Microglia Cells

Images of microglia cells were acquired with the INCell Analyzer 2000 Healthcare), using a 10× lens and excitation/emission filter pairs of 350 nm/455 nm (CellMask™ Red Stain) and 579 nm/624 nm (Hoechst dye). Images were analyzed with the GEHC INCell Developer Toolbox version 1.9. The Hoechst dye-stained cell nuclei were segmented using a "nuclear" segmentation type, with a set minimum target area of 30 µm² and set sensitivity of 75%. To minimize artifacts, any segmentation with less than 120 intensity units or area greater than 1000 µm² were excluded. The Cell Mask™ Red-stained whole microglia cells were segmented using an intensity segmentation type, with a set threshold between 200-4095 intensity units. The borders of adjacent contacting cells were resolved using the "clump breaking" segmentation post-processing that utilizes discrete nuclei as seeds. Only cells containing a nucleus within the cell body area were used further in the screening assay. All segmented nuclei and cells were then recorded as individual counts. Activated microglia cells were segmented by size into cells ≥800 µm². Dead cells were segmented into cells <150 µm².

When microglia are treated with doses of LPS of 1 ng or higher resulting in cell death, all cells that were labeled with CellMask™ Red Stain retained the label, but shrink to a cell surface area of 150 µm² or less. This is an important measurement that can be used to assess compound toxicity during screening for inhibitors of microglia activation.

Example 4

High Throughput Screen of a Test Compound Library

The SMDC/PHARMAKON (Microsource Discovery Systems, Gaylordville, Conn.) 1600 Collection is a library of known drugs that have reached development through clinical evaluation. Compounds from this library and 307 additional test compounds (the "Test Compound Library") were used in the inhibition of microglial activation screens. The screens measured the ability of the various individual compounds within this Test Compound Library to inhibit fibrin-induced microglia activation.

Individual compounds from the Test Compound Library were added to a final concentration of 10 µM to Fibrin-coated 384-well plates containing culture medium. After 1 hour of incubation of the plates in a 5% $CO_2$ incubator at 37°

C., primary rat microglia cells were plated at 6,000 cells per well in a 384-well plate. Cells were fixed after 48 hours of incubation in a 5% $CO_2$ incubator at 37° C. and labeled with CellMask Red™ and the nuclear Hoechst dye. Images were acquired using the INCELL Analyzer 2000 (GE Healthcare, United Kingdom) and analyzed with the INCELL Developer software, version 1.9. In the 384-well plate assay format, two columns each were reserved for the negative control (6 µg/ml coated Fibrin, 0% inhibition) and positive controls (uncoated wells, culture medium only, 100% inhibition), while 320 wells were used for test compounds.

Figure 1:
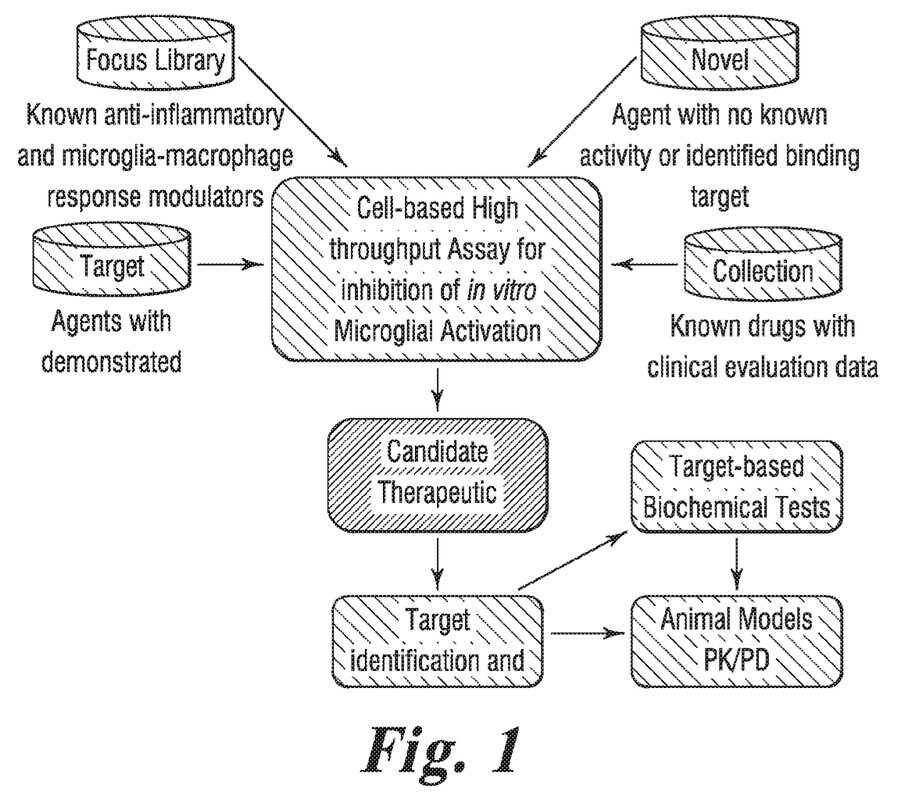
FIG. 1 is a flow chart illustrating the basic steps involved in using cell-based microglial activation assays to identify candidate therapeutic agents.
Figure 2:
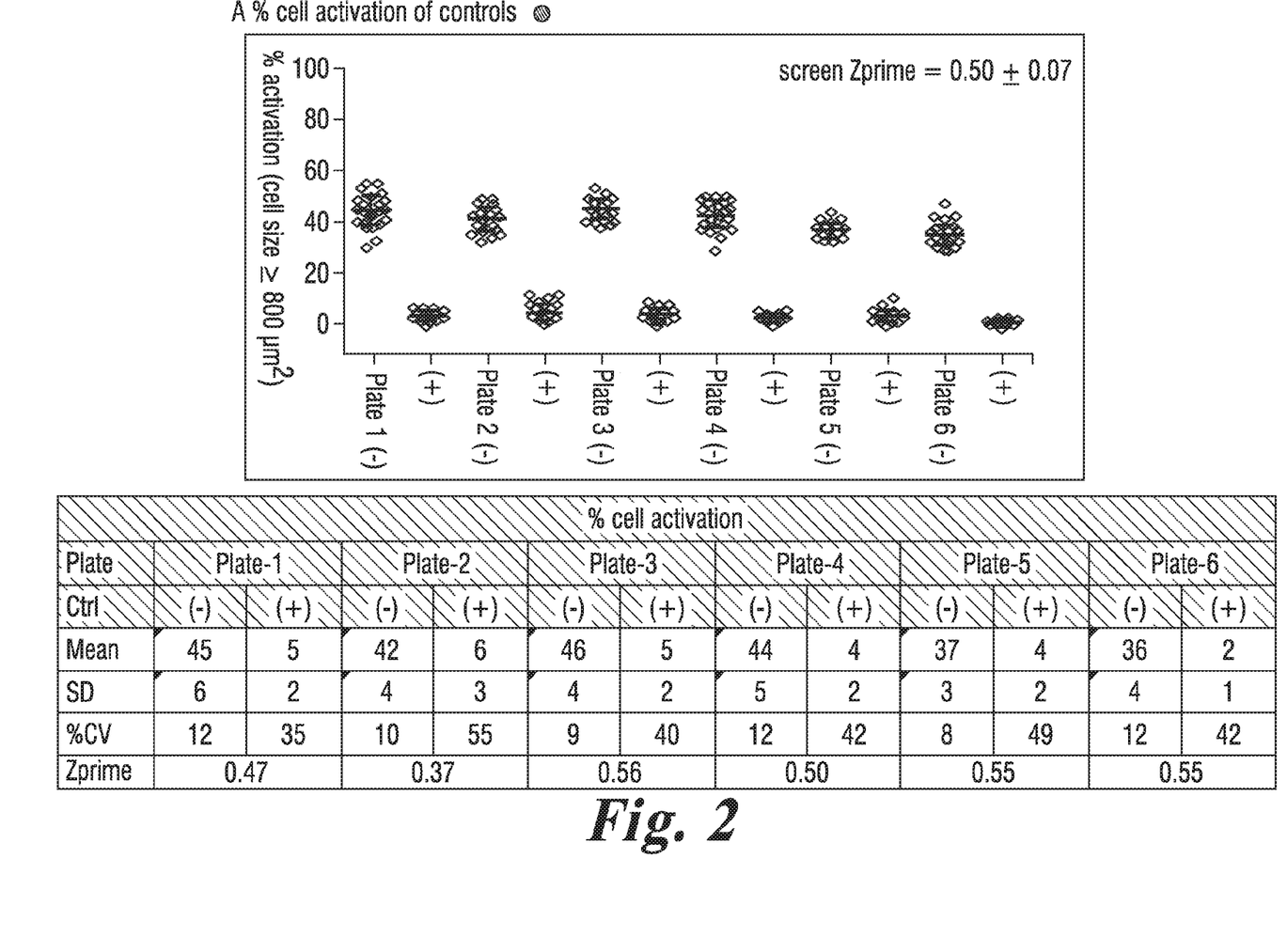
FIG. 2 is a graph showing the assay performance for a first screen of agents for inhibition of fibrin-induced microglia activation.
Figure 3:
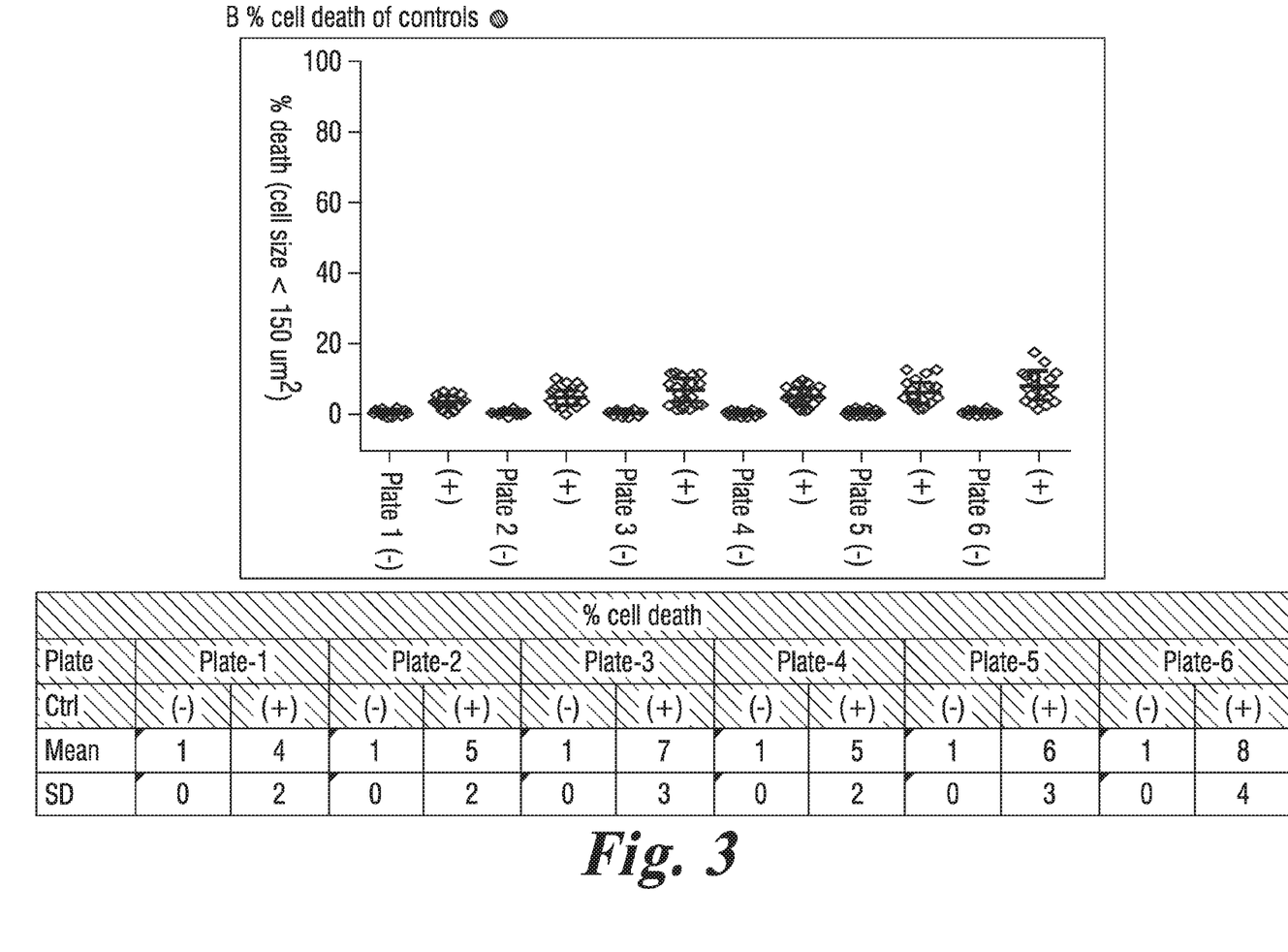
FIG. 3 is the summary of the amount of cell death within the normal range for test agents and negative and positive controls in the first screen of agents for inhibition of fibrin-induced microglia activation.

The assay performance for an initial screen of inhibition of fibrin-induced microglia activation is shown in FIGS. 2 and 3. Z' values measured were between 0.47 and 0.56 for the six assay plates (FIG. 2), and the amount of cell death within the normal range for both negative and positive controls (FIG. 3).

Figure 4:
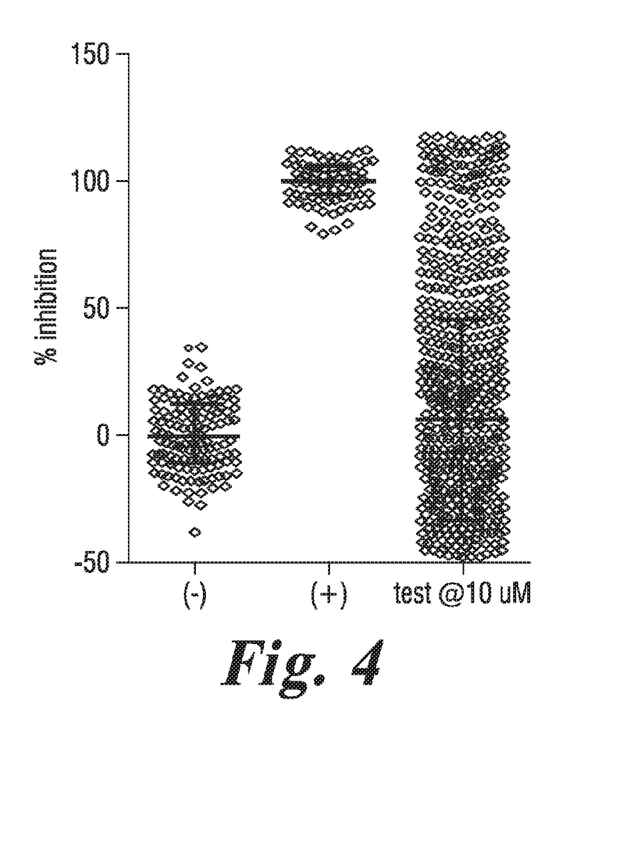
FIG. 4 is a plot showing the distribution of percent inhibition values for tested agents and positive and negative controls in the HTS of agents that inhibit in vitro fibrin-activation of microglia.
Figure 5A:
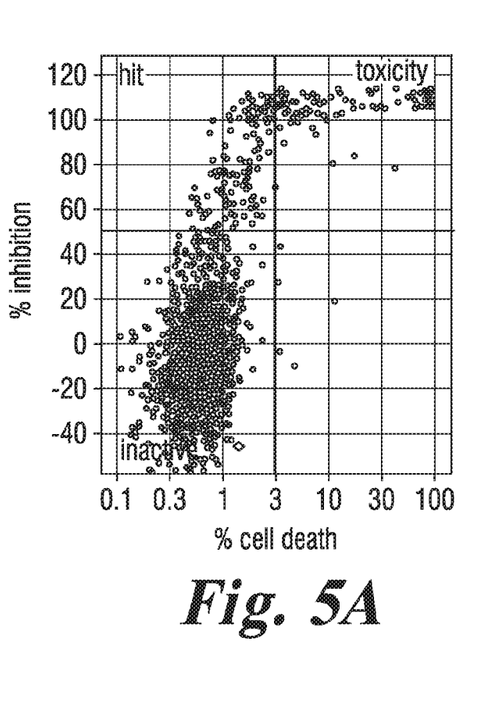
FIG. 5A is a plot showing the range of activity of the tested agents in the fibrin inhibition assay.
Figure 5B:
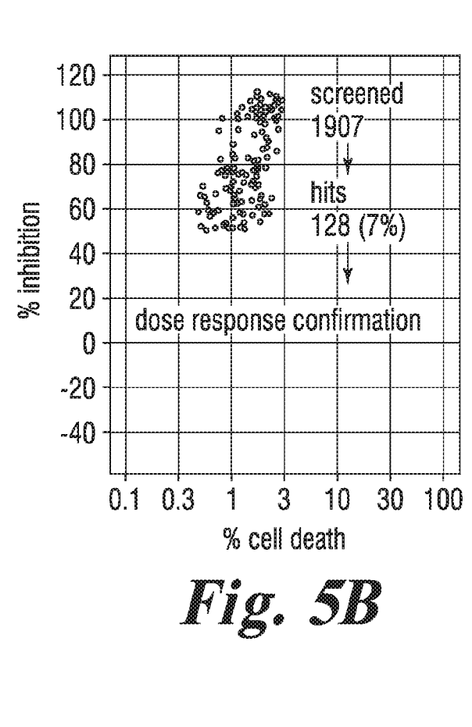
FIG. 5B is a plot showing the dose response curve of the 128 identified "hits" from this assay.

The criteria for the selection of candidate therapeutic agents in this experiment were ≥50% inhibition of fibrin-induced microglial activation and less than 3% cell death to exclude toxic compounds. The results are shown in FIGS. 4, 5A and 5B. FIG. 4 is a plot showing the distribution of percent inhibition values for compounds and positive and negative controls. The screening of 1907 compounds resulted in the selection of 128 candidate therapeutic agents in total which met the criteria for 50% or greater inhibition of fibrin-induced microglial activation and less than 3% cell death (a 7% hit rate) (FIG. 5A). The 128 selected candidate therapeutic agents were used to generate dose response curves for inhibition of microglial activation (FIG. 5B).

These test agents represent candidate therapeutic agents for the inhibition of microglia cell activation in vivo, as they demonstrate efficacy in the physiologically-predictive fibrin-induced activation of microglia in the assay systems of the invention.

Example 5

Inhibition of LPS-Induced Microglia Activation

Figure 6:
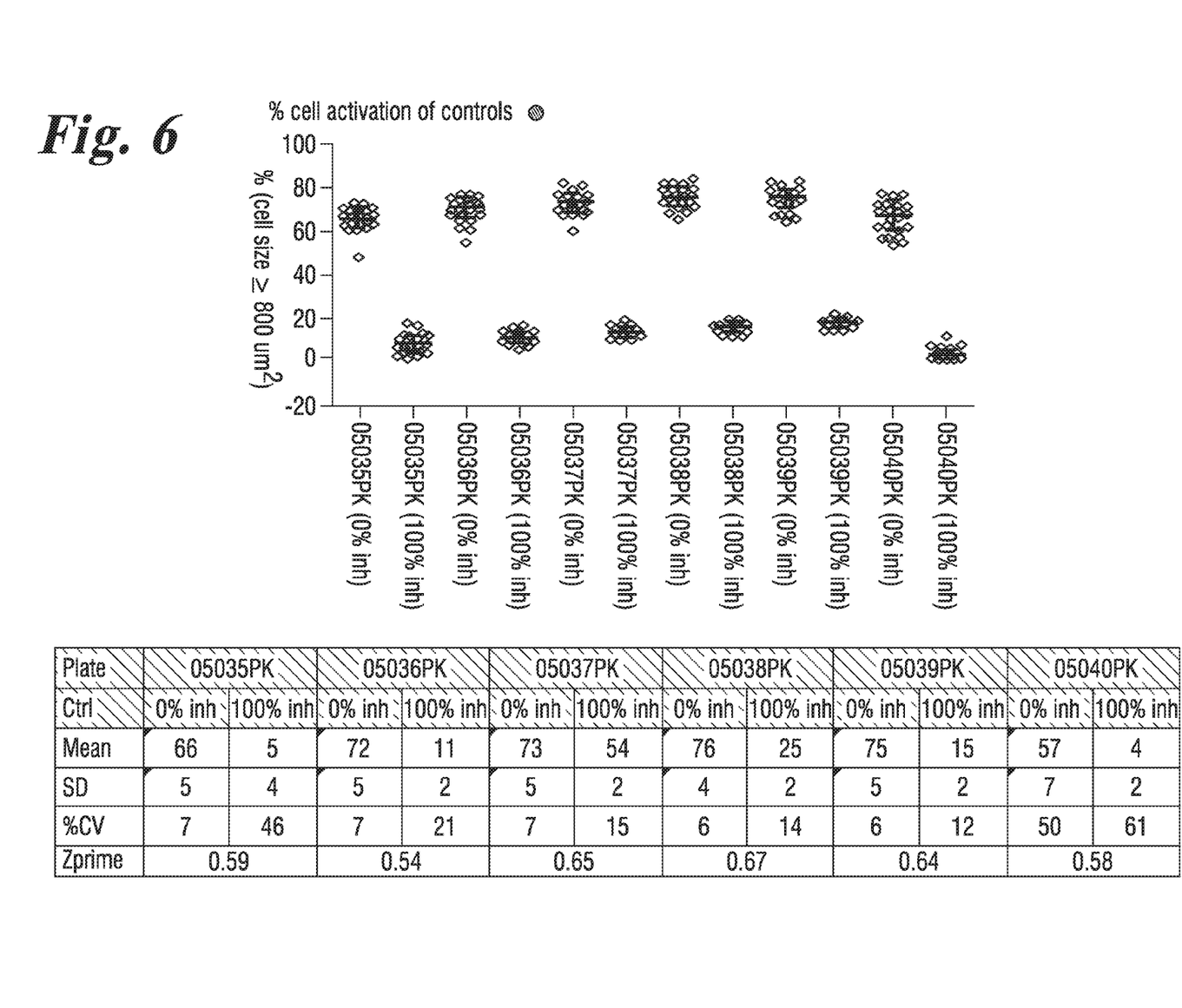
FIG. 6 is a graph showing the assay performance for a first screen of agents for inhibition of LPS-induced microglia activation. Z' values for the inhibitors of LPS-induced percent microglia activation were between 0.47 and 0.56 for the six assay plates.
Figure 7:
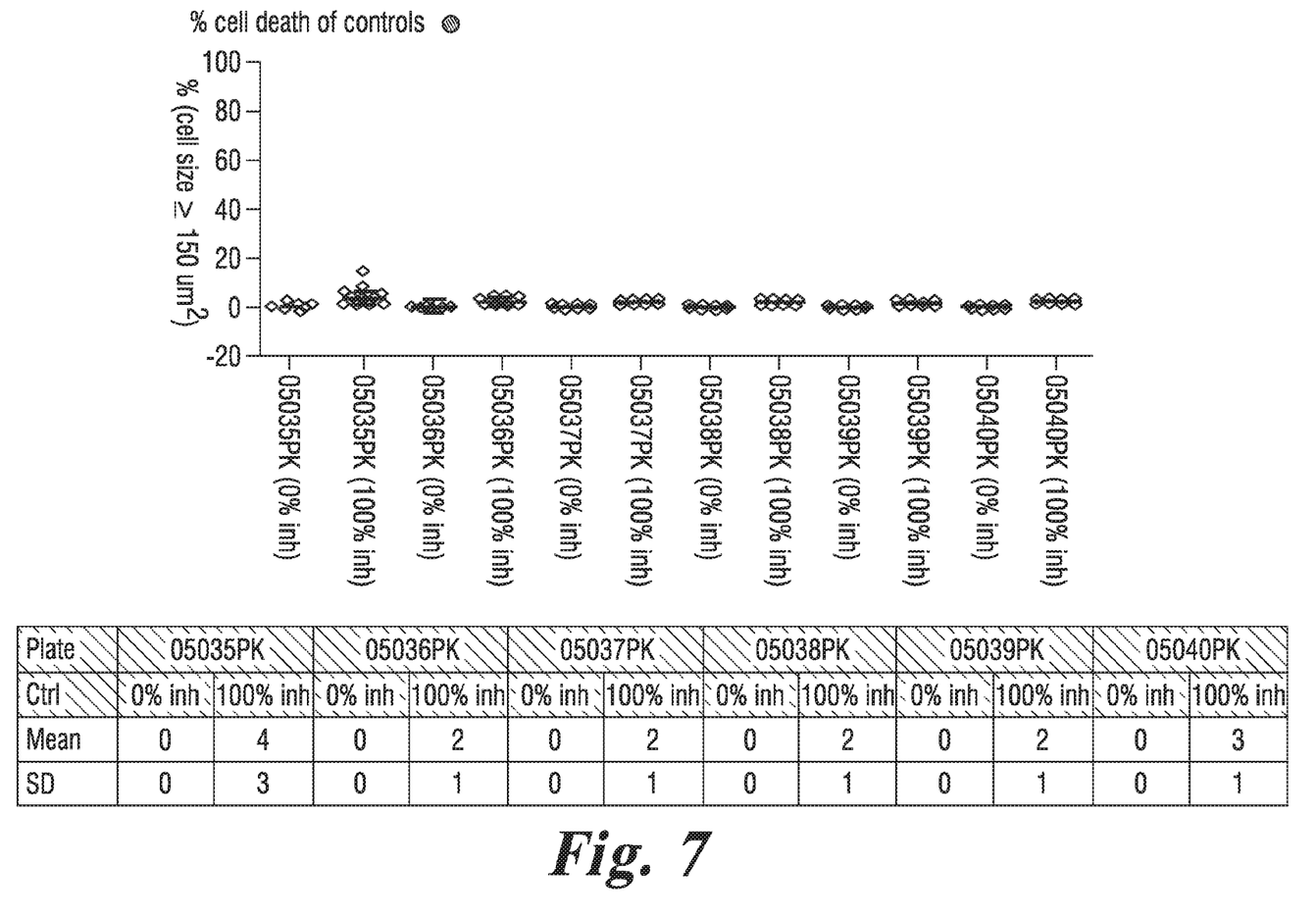
FIG. 7 is the summary of the amount of cell death within the normal range for test agents and negative and positive controls in the HTS of agents that inhibit in vitro LPS-activation of microglia.

Primary rat microglia cells were plated into PDL-coated 384 well plates (Greiner, Germany) at 6,000 cells per well and incubated for an hour. After 1 hour, compounds from the Test Compound Library were added at a concentration of 10 p, M, 1 hour prior to the addition of LPS at a concentration of 500 pg/mL This concentration was chosen based on a dose response curve for LPS-induced microglia activation as the optimal dose for maximum morphological activation. Cells were fixed after 48 hrs of incubation in a 5% CO2 incubator at 37° C. and labeled with CellMask™ Red Stain and nuclear Hoechst dye. Images were acquired using the INCeLL Analyzer 2000 (GE Healthcare, United Kingdom) and analyzed with the INCELL Developer software, version 1.9. The assay performance for the pilot screen of LPS-induced microglial activation is shown in FIGS. 6 and 7. Z' values were between 0.58 and 0.67 for the six assay plates (FIG. 6) and the amount of cell death within the normal range for both negative and positive controls (FIG. 7).

Figure 8A:
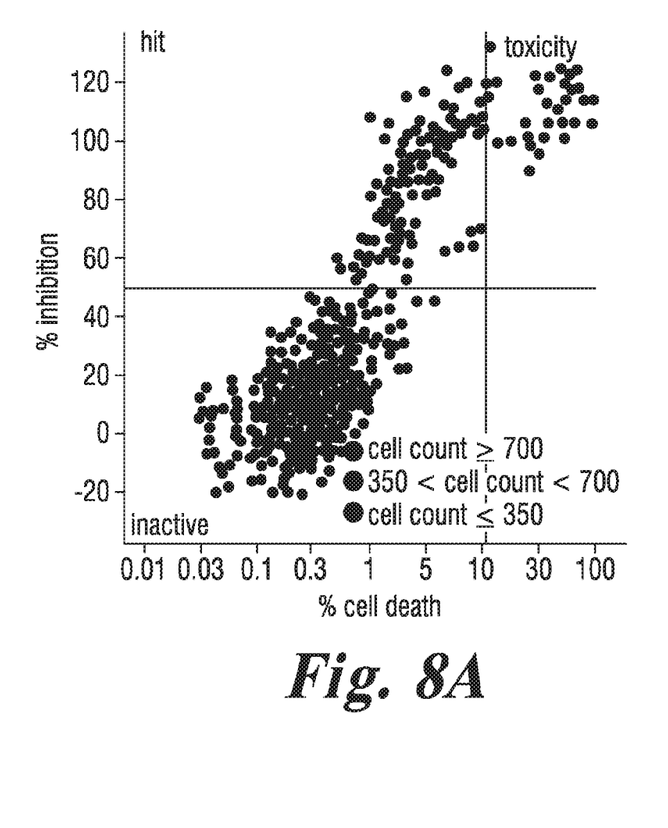
FIG. 8A is a plot showing the range of activity of the tested agents in the microglia LPS-activation inhibition HTS assay.
Figure 8B:
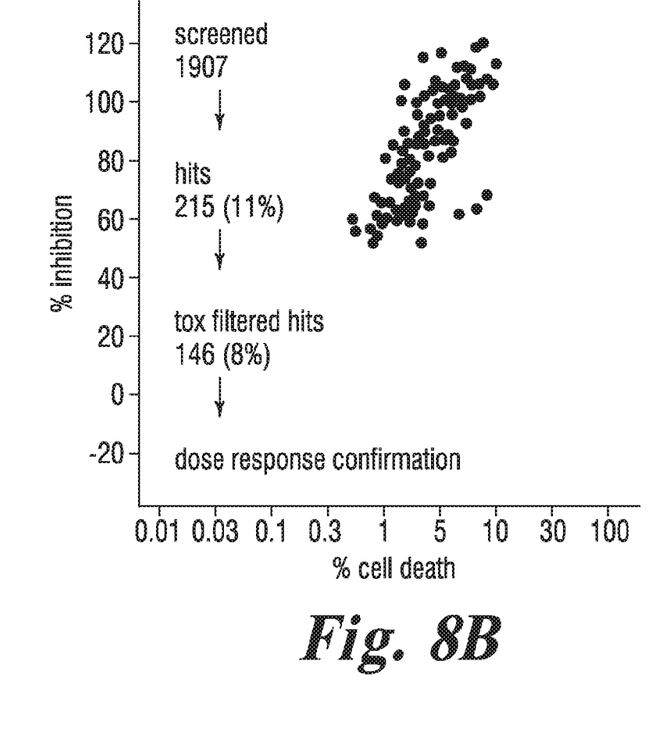
FIG. 8B is a plot showing the dose response curve of the 146 identified "hits" from this assay.

The criteria for the selection of candidate therapeutic agents were ≥50% inhibition of LPS-induced microglial activation and less than 10% cell death to exclude toxic compounds. The screening of 1907 test agents from the Test Compound Library resulted in 215 hits in total meeting the 50% inhibition criterion (an 11% hit rate) (FIG. 8A). After removing test agents that were toxic, 146 compounds (an 8% hit rate) met the criteria for 50% or greater inhibition of LPS induced microglial activation and less than 10% cell death (FIG. 8B). These test agents represent candidate therapeutic agents for the inhibition of microglia cell activation in vivo, as they demonstrate efficacy in the physiologically predictive LPS-microglia activation assay systems of the invention.

Example 6

Figure 9:
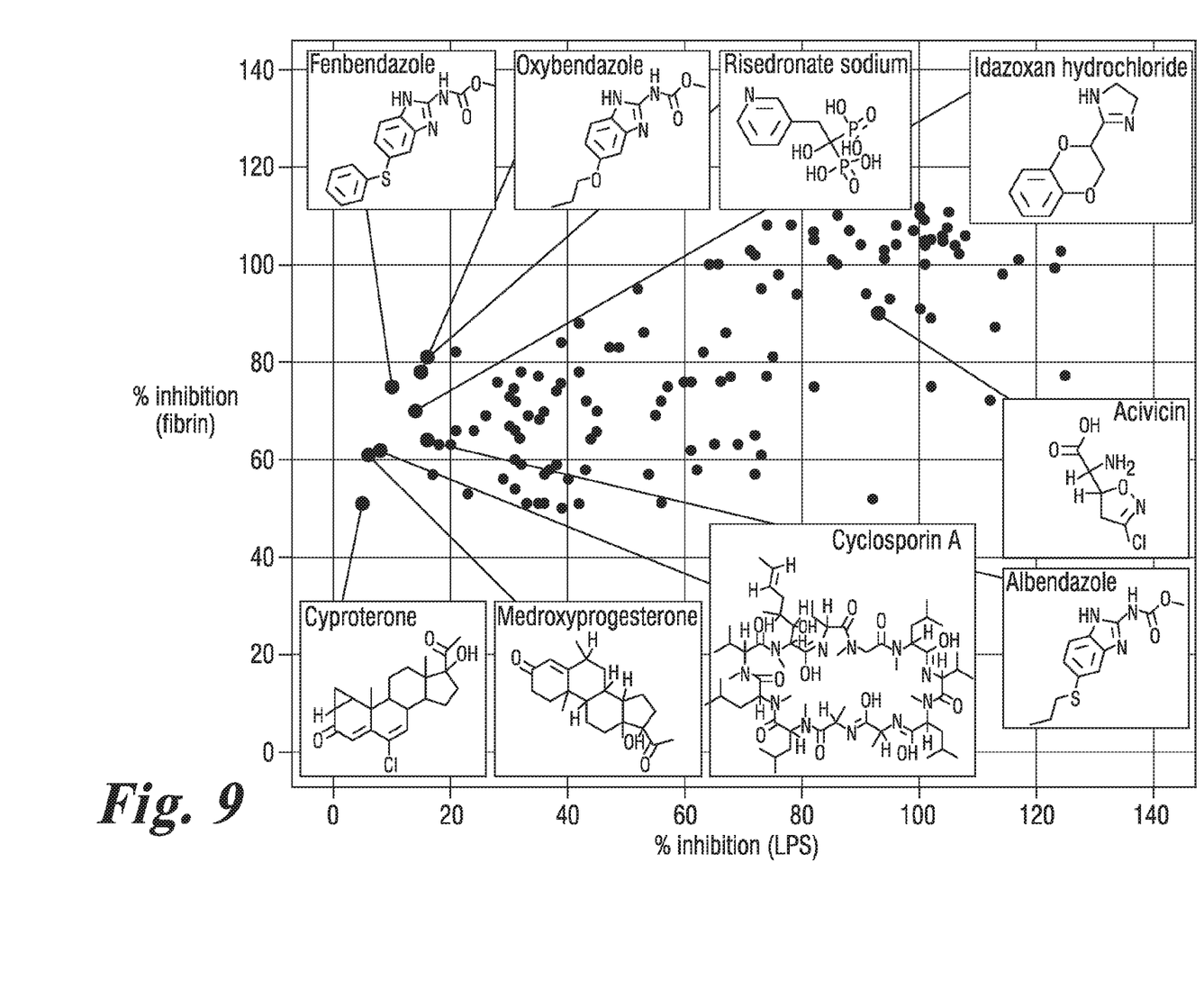
FIG. 9 shows the distribution of hit compounds efficacious against both Fibrin and LPS-induced microglia activation.

Test Agents that Inhibit Both Fibrin-Induced and LPS-Induced Microglia Activation Screens FIG. 9 shows a distribution of test agents efficacious against both in vitro fibrin-induced and LPS-induced microglia activation. Compounds distributing to the left top side of the graph were demonstrated to have greater efficacy in inhibiting fibrin-induced microglia activation, whereas test agents on the right bottom were demonstrated to be more efficacious in inhibiting LPS-induced activation. Several compounds in the top right of the graph seem to equally inhibit both mechanisms of activation. Such test agents are particularly interesting as candidate therapeutic agents for the inhibition of microglia cell activation in vivo, as they demonstrate efficacy in two physiologically predictive in vitro assay systems.

The preceding merely illustrates the principles of the invention. It will be appreciated that those skilled in the art will be able to devise various arrangements and equivalents which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A high-throughput cell-based assay for simultaneously identifying toxicity and the inhibition of microglia activation in vivo for identification of one or more candidate therapeutically active agents, comprising
    providing a panel comprising fibrin and in vitro activated microglial cells, wherein the microglial cells are activated by in vitro exposure to LPS;
    contacting said panel of microglial cells with one or more test agents;
    identifying one or more test agents that inhibit microglial activation, wherein inhibition of in vitro microglial cell activation is predictive of therapeutic activity of the test agents in vivo; and
    simultaneously determining the level of cell death caused by the identified test agents that inhibited microglial activation;
    wherein the level of cell death caused by the test agents is associated with lack toxicity of the agents in vivo;
    wherein activation of microglial cells and death of microglial cells are simultaneously determined by imaging and measurement of cell surface, wherein activated microglial cells have a cell surface area of ≥800 µm$^2$ and dead microglial cells have a surface area of 150 µm$^2$ or less; and wherein the one or more test agents that exhibit both inhibition of the activation of microglial cells and lack of toxicity are candidate therapeutically active agents for inhibition of microglia activation in vivo.

2. The assay of claim 1, wherein the one or more test agents comprise agents with demonstrated affinity to targets involved in microglia activation.

3. The assay of claim 1, wherein the one or more test agents comprise agents with no known activity or identified binding target.

4. The assay of claim 1, wherein the one or more test agents comprise known drugs with clinical evaluation data.

5. The assay of claim 1, wherein the one or more test agents comprise known anti-inflammatory agents and microglia-macrophage response modulators.

6. The assay of claim 1, wherein the fibrin mimics the biochemical and proinflammatory properties of fibrin matrices found in vivo during pathological conditions.

* * * * *